United States Patent
Fang et al.

(10) Patent No.: US 10,024,847 B2
(45) Date of Patent: Jul. 17, 2018

(54) HYDROPHILIC FILM FOR EX VIVO MEMBRANE

(71) Applicant: ETERNAL MATERIALS CO., LTD., Kaohsiung (TW)

(72) Inventors: Mei-Yen Fang, Kaohsiung (TW); Tu-Yi Wu, Kaohsiung (TW)

(73) Assignee: ETERNAL MATERIALS CO., LTD., Kaohsiung (TW)

( * ) Notice: Subject to any disclaimer, the term of this patent is extended or adjusted under 35 U.S.C. 154(b) by 0 days.

(21) Appl. No.: 15/134,652

(22) Filed: Apr. 21, 2016

(65) Prior Publication Data

US 2016/0312058 A1 Oct. 27, 2016

(30) Foreign Application Priority Data

Apr. 24, 2015 (TW) .............................. 104113300 A

(51) Int. Cl.
| | |
|---|---|
| G01N 33/66 | (2006.01) |
| C09D 175/08 | (2006.01) |
| C08G 18/79 | (2006.01) |
| G01N 33/52 | (2006.01) |
| C08G 18/48 | (2006.01) |
| C08G 18/66 | (2006.01) |
| C08G 18/81 | (2006.01) |
| C08G 18/08 | (2006.01) |
| C08G 18/28 | (2006.01) |
| C08G 18/32 | (2006.01) |

(52) U.S. Cl.
CPC ....... *G01N 33/526* (2013.01); *C08G 18/0814* (2013.01); *C08G 18/285* (2013.01); *C08G 18/289* (2013.01); *C08G 18/3206* (2013.01); *C08G 18/4833* (2013.01); *C08G 18/6677* (2013.01); *C08G 18/792* (2013.01); *C08G 18/8116* (2013.01); *C09D 175/08* (2013.01); *G01N 33/525* (2013.01); *G01N 33/66* (2013.01)

(58) Field of Classification Search
None
See application file for complete search history.

(56) References Cited

U.S. PATENT DOCUMENTS

| | | | | |
|---|---|---|---|---|
| 6,080,812 A | * | 6/2000 | Morishima | .......... C08G 18/706 524/589 |
| 2009/0264587 A1 | * | 10/2009 | Blum | ................. C08G 18/0823 524/591 |

FOREIGN PATENT DOCUMENTS

TW 201404810 A 2/2014

OTHER PUBLICATIONS

Abstract of CN 102384931 A (2012).*
Office Action from TW application No. 104113300 dated Oct. 15, 2015.

* cited by examiner

*Primary Examiner* — Frank D Ducheneaux
(74) *Attorney, Agent, or Firm* — Shimokaji IP

(57) ABSTRACT

The present invention provides a hydrophilic film for an ex vivo membrane, which includes:
  a substrate; and
  a hydrophilic coating located on at least one surface of the substrate and formed by a hydrophilic composition, in which the hydrophilic composition includes:
  (a) a reactive adhesive;
  (b) a surfactant having reactivity; and
  (c) optionally a polyol.

16 Claims, 1 Drawing Sheet

HYDROPHILIC FILM FOR EX VIVO MEMBRANE

BACKGROUND OF THE INVENTION

1. Field of the Invention

The present invention relates to a hydrophilic film for an ex vivo membrane and the ex vivo membrane.

2. Description of the Related Art

Various ex vivo test strips are being actively developed. Those strips use urine, stool, blood, saliva or other bodily fluids as samples for detecting various health indexes or physiological conditions of humans. Improving the stability and accuracy of test strips is a target that manufacturers are continually striving to accomplish. Blood glucose test strips receive the broadest attention. Annual increases in diabetic populations are driving industrial research on improving blood glucose test strips.

Generally, the ex vivo test strip has a structure as shown in FIG. 1, in which a hydrophilic film 11 is combined with a middle barrier layer 12, to form a flow channel 13 which allows a test fluid to enter a detection layer 14. The hydrophilic film 11 is composed of a substrate 111 (which is generally a transparent plastic substrate) and a hydrophilic layer 112.

The structure of the ex vivo test strip is further illustrated in FIG. 2. As shown in FIG. 2, the function of the hydrophilic film 11 is to promote the delivery of the test fluid, whereby the test fluid enters a detection region 15 in the detection layer 14 via the flow channel 13, while the detection region 15 is protected against contamination and isolated from external interference. Also, the hydrophilic film 11 has the function of providing measurement stability. To avoid failure of the ex vivo test strip due to degradation from contact with ambient moisture, oxygen, or UV light, the hydrophilic film 11 is required to have good resistance to humidity and heat, high hydrophilicity, and other properties. Moreover, the volume of the flow channel 13 needs to remain constant, to ensure measurement stability. Therefore, the hydrophilic layer 112 in the hydrophilic film should be firmly adhered to the substrate 111.

The materials of the hydrophilic layer commonly used in the art mainly include hydrophilic resins or surfactants. The surfactants (e.g. a sulfonate compound) have the advantages of good hydrophilicity and a relatively low amount to be used. However, the surfactants are susceptible to environmental conditions causing degradation. Therefore, a hydrophilic resin with good hydrophilicity and wettability and high resistance to humidity and heat may be used in combination with a surfactant as the materials of a hydrophilic layer.

At present, the commercially available hydrophilic film used for medical diagnosis is exemplified by the product 9962 from 3M Inc. The hydrophilic layer of the hydrophilic film includes a polyvinylidene chloride coating comprising an alkylbenzyl sulfonate based surfactant. Although a biological fluid may be delivered by the diagnosis strip made from such a hydrophilic film, the product is shown through testing to have significant defects such as inadequate uniformity, delivery rate and anti-aging stability.

Other commercially available hydrophilic films include ARflow 90128 and ARflow 90469 from Adhesives Research Inc. These products include a polyester film coated with a composition comprising a thermoplastic co-polyester and a surfactant, and having a mode of action similar to the above-mentioned product from the 3M Inc. To avoid non-uniformity, quite a large amount of surfactant (about 5 to 8%) is added, causing the hydrophilic coating to have a waxy surface. Because a sufficient bonding strength cannot be attained when the coating is bound to a pressure sensitive tape, delamination of the assembly frequently occurs during the fabrication of the test strip.

In addition to the above-mentioned defects, the hydrophilic film is required to be patterned during the manufacture of an ex vivo membrane from a conventional hydrophilic film, resulting in frequent failure of the hydrophilic coating due to fouling of the surface of the hydrophilic coating by printing ink or sweaty hands. Therefore, the hydrophilic coating should be shielded or covered with an additional protective layer, making the process troublesome and costly.

Consequently, the inventors provide a novel hydrophilic film for an ex vivo membrane, by which the aforesaid problems are effectively solved. The hydrophilic film according to the present invention has a special hydrophilic coating having a robust bonding strength to the substrate, by which the stripping of the hydrophilic layer occurring during processing can be avoided, and which is beneficial to subsequent processing and manufacturing, thereby simplifying the process steps and reducing cost. Moreover, the present invention has excellent hydrophilicity and resistance to humidity and heat, whereby the ineffectiveness of the ex vivo membrane resulting from degradation and failure of the hydrophilic film due to exposure to adverse environmental conditions can be avoided. Therefore, the shelf life of the ex vivo membrane can be effectively extended by the hydrophilic film of the present invention.

SUMMARY OF THE INVENTION

The present invention mainly aims at providing a hydrophilic film for an ex vivo membrane. The hydrophilic film may be directly processed with subsequent functional layers to form the ex vivo membrane and has excellent hydrophilicity and hydrophilicity maintaining ability.

To achieve the above purpose, the present invention provides a hydrophilic film for an ex vivo membrane, which comprises:

a substrate; and a hydrophilic coating located on at least one surface of the substrate and formed by a hydrophilic composition, wherein the hydrophilic composition comprises:

(a) a reactive adhesive;
(b) a surfactant having reactivity; and
(c) optionally a polyol.

BRIEF DESCRIPTION OF THE DRAWINGS

The invention will be described according to the appended drawings, in which.

PREFERRED EMBODIMENT OF THE PRESENT INVENTION

Figure 1:
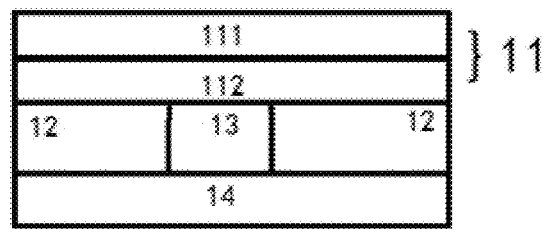
FIG. 1 is a schematic structural view of an ex vivo test strip.
Figure 2:
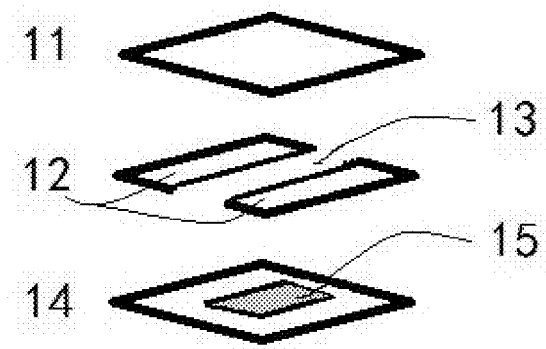
FIG. 2 is another schematic structural view of an ex vivo test strip.

The applications of the ex vivo membrane of the present invention are diverse, for example, ex vivo test strips, wound dressings or band-aids. The prepared hydrophilic coatings vary in thickness depending on different applications. For example, in an ex vivo test strip, the thickness of the hydrophilic coating is 10 nm to 100 μm. If the thickness of the hydrophilic coating is less than 10 nm, it cannot provide effective hydrophilicity. If the thickness of the hydrophilic coating is more than 100 μm, the adhesion of the substrate to the hydrophilic coating is poor and unfavorable to subsequent processing.

Substrate

The substrate used in the present invention is preferably a plastic substrate, which is not particularly limited, and may be one known to persons of ordinary skill in the art of the present invention, for example, but not limited to, polyester resin, such as polyethylene terephthalate (PET) or polyethylene naphthalate (PEN); polyacrylate resin, such as polymethyl methacrylate (PMMA); polyolefin resin, such as polyethylene (PE) or polypropylene (PP); polycycloolefin resin; polyamide resins, for example, nylon 6, nylon 66 or MXD nylon (m-xylene diamine/adipic acid copolymer); polyimide resin; polycarbonate resin; polyurethane resin; polyvinylchloride (PVC); triacetyl cellulose (TAC); polylactic acid; substituted olefinic polymers, for example, polyvinyl acetate or polyvinyl alcohol; copolymer resins, for example, EVA, ethylene/vinyl alcohol copolymer, or ethylene/tetrafluoroethylene copolymer; or a combination thereof. Preferably, the substrate is polyester resin, polyacrylate resin, polyimide resin or a combination thereof. More preferably, the substrate is polyethylene terephthalate. The thickness of the substrate is not particularly limited, and is generally about 15 microns (μm) to about 500 microns (μm), and preferably about 20 microns (μm) to about 300 microns (μm), depending on the requirements of the product to be produced.

Hydrophilic Composition

In the hydrophilic composition mentioned in the present invention, the content of the reactive adhesive is 10 to 60 wt %, based on the total solid content of the composition; the content of the surfactant is 5 to 90 wt %, based on the total solid content of the composition; and the content of the polyol is 0 to 85 wt % based on the total solid content of the composition. The solid content is defined as the content of non-volatile (NV) ingredients.

Solvent

The solvent used in the hydrophilic composition mentioned in the present invention is one that can prevent agglomeration of the composition, thereby facilitating convenience of application of the hydrophilic coating while avoiding the tendency to produce a non-uniform coating. The solvent may be selected from an ester, alcohol or ether solvent, or water, or a mixture thereof, preferably an ester, alcohol or ether solvent or a mixture thereof (that is, containing no water), and more preferably an ester or ether solvent. According to some specific embodiments of the present invention, the solvent is, for example ethyl acetate, dimethyl ether or diethyl ether.

The content of the solvent used in the present invention is preferably 90-99.9% based on the total weight of the hydrophilic composition. When the solvent content is below 90%, a non-uniform coating may easily occur.

Reactive Adhesive

The reactive adhesive in the hydrophilic composition mentioned in the present invention may be selected from the group consisting of an isocyanate compound, a melamine compound, and a mixture thereof. The isocyanate compound may bear an alkyl group, a phenyl group, a phosphoric acid functional group, a sulfonic acid functional group, or an acrylate functional group, and may be a mono-, di-, or polyisocyanate (containing three or more isocyanate groups) compound. The above-mentioned alkyl or phenyl group may also be an alkylene or phenylene, depending on the substituted positions thereon.

The di-, or polyisocyanate compound is preferred. The isocyanate compound containing an alkyl group may be selected from the group consisting of, for example, but not limited to, hexamethylene diisocyanate, 1,4-diisocyanatocyclohexane, 1-isocyanato-3,3,5-trimethyl-5-isocyanatomethylcyclohexane, 4,4'-diisocyanatodicyclohexylmethane, 4,4'-diisocyanatodicyclohexylpropane, and a mixture thereof. The commercially available product includes, for example, Desmodur N3300 or Desmodur N3390.

The isocyanate compound containing a phenyl group may be selected from the group consisting of, for example, but not limited to, 1,4-diisocyanatobenzene, 2,4-diisocyanatotoluene, 2,6-diisocyanatotoluene, 4,4'-diisocyanatodiphenylmethane, 2,2'- and 2,4'-diisocyanatodiphenylmethane, tetramethyl benzene dimethyl diisocyanate, p-dimethylbenzene diisocyanate, and a mixture thereof. The commercially available product includes, for example, Desmodur L-75.

The isocyanate compound containing a phosphoric functional group includes, for example, but is not limited to, triisocyanate triphenylthiophosphate

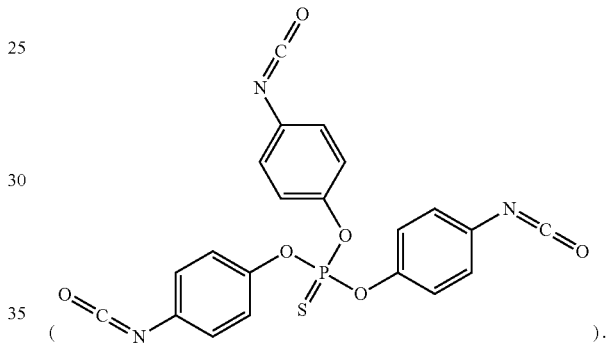

The isocyanate compound containing a sulfonic acid functional group includes, for example, the commercially available Bayhydur XP 2655.

The isocyanate compound containing an acrylate functional group includes, for example, the commercially available product Karenz AOI.

The reactive adhesive used in the present invention is preferably selected from the group consisting of an alkyl-containing isocyanate, a phenyl-containing isocyanate and a mixture thereof; and more preferably from the group consisting of an alkyl-containing triisocyanate, a phenyl-containing triisocyanate and a mixture thereof.

The melamine compound may be a commercially available product, for example, Cymel 202, Cymel 203, Cymel 254, Cymel 323, Cymel 325, Cymel 327, Cymel 328, Cymel 370, Cymel 380, Cymel 385, Cymel 1116, Cymel 1130, Cymel 1133, Cymel 1141, Cymel 1161, Cymel 1168 or Cymel 3020 manufactured by Cytec Corp.; or ETERMINO 9212 ETERMINO 9216, ETERMINO 9223, ETERMINO 9226, ETERMINO 9228, ETERMINO 9229, ETERMINO 9603 manufactured by Eternal Material Co., Ltd.; or a combination thereof.

The reactive adhesive may form a polymer with a surfactant having reactivity. Compared with the conventional hydrophilic composition containing a surfactant alone, the hydrophilic composition of the present invention can provide desirable physical and chemical properties (resistance to humidity and heat), to facilitate the maintenance of the hydrophilicy of the hydrophilic coating.

The reactive adhesive of the present invention is used in an amount of 10 to 60 wt %, preferably 13 to 55 wt %, and more preferably 15 to 45 wt %, based on the total solid content of the composition. When the amount is less than 10 wt %, due to insufficient cross-linking of the coating, the hydrophilic ingredient (surfactant) in the coating cannot be effectively immobilized and is thus in a free state, leading to poor transparency and poor hydrophilicity maintaining ability of the coating. When the amount is higher than 60 wt %, due to the inadequate relative proportion of the hydrophilic ingredient (surfactant), the overall hydrophilicity of the coating is poor.

Surfactant Having Reactivity

The surfactant having reactivity mentioned in the present invention may be selected from the group consisting of an ionic emulsifying agent, a nonionic emulsifying agent, and a mixture thereof. The surfactant may contain a reactive functional group selected from the group consisting of amino, hydroxyl, and a combination thereof, and preferably hydroxyl.

The above-mentioned ionic emulsifying agent has a cationic group and/or an anionic group, wherein the cationic group may include an ammonium or sulfonium group, and the anionic group can be selected from the group consisting of a sulfonic acid group, a phosphoric acid group, a carboxylic acid group, and a combination thereof.

The reactive group of the ionic emulsifying agent may exist either in the cationic group or in the anionic group, and preferably in the cationic group. Therefore, the cationic group of the ionic emulsifying agent may comprise amino, hydroxyl, or a combination thereof.

The ionic emulsifying agent may have a cationic group as shown below:

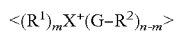

where $X^+$ is $N^+$ or $S^+$; G is a divalent organic group, preferably a $C_{1-6}$ alkylene group, and more preferably a $C_{1-4}$ alkylene group; $R^1$ is an inert or nonreactive group, for example, but not limited to, alkyl, aryl or cycloalkyl; $R^2$ is —OH or —NH$_2$; when $X^+$ is $N^+$, n is 4 and m is an integer ranging from 0 to 3; and when $X^+$ is $S^+$, n is 3 and m is an integer ranging from 0 to 2.

Therefore, the ionic emulsifying agent may have a cationic group as shown below:

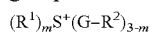

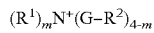

where G, $R^1$, $R^2$ and m are as defined above.

The ionic emulsifying agent may have a cationic group as shown below:

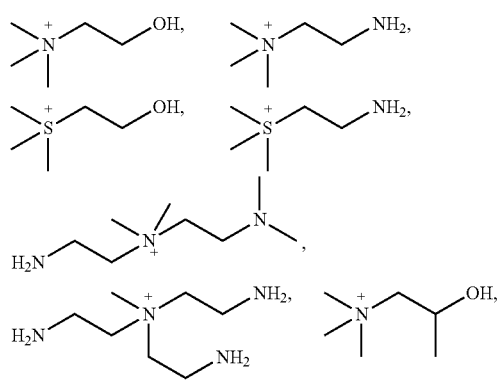

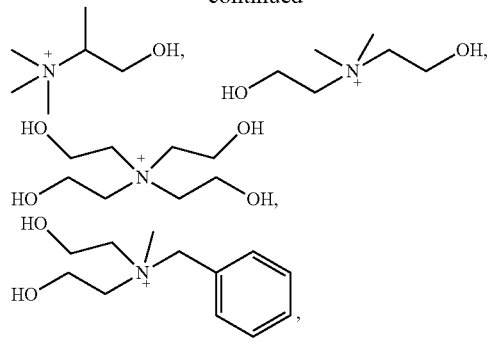

and a combination thereof.

The ionic emulsifying agent may have an anionic group as shown below:

$F^-$, $Cl^-$, $Br^-$, $I^-$, or $OH^-$.

The ionic emulsifying agent may also have an anionic group including those selected from the group consisting of a sulfonic acid group, a phosphoric acid group, a carboxylic acid group, and a combination thereof, or a group derived therefrom. The above-mentioned anionic group may further contain a substituent that is hydrogen or a monovalent organic group, optionally an organic group with alkyl, alkoxy, amino, hydroxyl, aryl, or a combination thereof. The anionic group in the present invention can for example be:

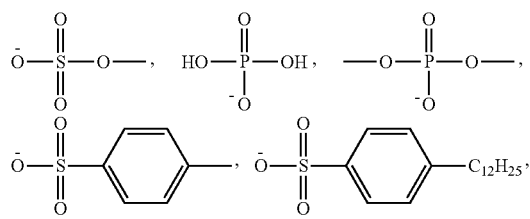

bis(2-ethylhexyl)succinate sulfonate, formate, acetate, benzoate, or a combination thereof.

The nonionic emulsifying agent used in the present invention may be a compound having a siloxanyl group or a polysiloxanyl group that preferably has no alkoxy group.

In an embodiment of the present invention, the nonionic emulsifying agent has a molecular weight (MW) of below 2000, preferably below 1500, and more preferably below 1000.

The nonionic emulsifying agent may have the formula below:

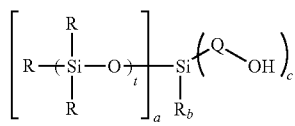

where $a+b+c=4$; a, b and c are integers, and c is an integer from 1 to 3; t is an integer from 1 to 20; each R is independently an inert/nonreactive group selected from alkyl, aryl, and cycloalkyl; and Q is a linking group selected from alkyl, an ether group, aryl, cycloalkyl, or a combination thereof.

The nonionic emulsifying agent may have the formula below:

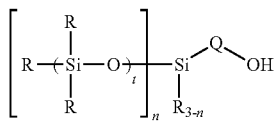

where n is an integer from 0 to 2, and t is an integer from 1 to 20;

R is an inert/nonreactive group selected from alkyl, aryl, cycloalkyl, or the like;

Q is a linking group selected from alkyl, an ether group, aryl, cycloalkyl, or a combination thereof. The nonionic emulsifying agent may be a commercially available product, for example, 7608 provided by Momentive.

The content of the surfactant having reactivity of the present invention is 5 to 90 wt %, based on the total solid content of the composition. When the hydrophilic composition contains a polyol, the content of the surfactant is preferably 5 to 50 wt %, and more preferably 10 to 40 wt %. When the hydrophilic composition contains no polyol, the content of the surfactant is preferably 50 to 90 wt %, and more preferably 60 to 85 wt %.

Polyol

The hydrophilic composition mentioned in the present invention optionally comprises a polyol. The polyol suitable for the present invention is not particularly limited, and may be selected from the group consisting of a polyether polyol, a polyester polyol, a polycarbonate polyol, a polylactone polyol, a polyamide polyol, and a combination thereof, and preferably a polyether polyol, such as polyethylene glycol.

The polyol mentioned in the present invention is used in an amount of 0 to 85 wt %, and preferably 15 to 65 wt %, based on the total solid content of the hydrophilic composition.

Additives

The hydrophilic composition of the present invention may further contain a curing agent, a curing accelerator, an anti-oxidant, a leveling agent, an inorganic compound, or a combination thereof.

The above-mentioned inorganic compound is preferably a particulate compound, that is, inorganic particles. The species of the inorganic particles includes, but is not limited to, magnesium oxide, silicon dioxide, titanium dioxide, zirconium oxide, ferric oxide, aluminum oxide, calcium sulfate, barium sulfate or a mixture thereof, and preferably silicon dioxide. The inorganic compound preferably has a nano grade particle size. The addition of the inorganic compound may further increase the hydrophilicity of the hydrophilic composition.

The hydrophilic coating formed by the hydrophilic composition of the present invention has a thickness of 10 nm to 100 microns and preferably 10 nm to 5 microns.

The hydrophilic film of the present invention may be combined with other functional layers to prepare various ex vivo membranes. Taking a fluid test strip for example, its conventional structure comprises an insulating substrate; electrodes (including a working electrode and a reference electrode) provided on the substrate; an insulating height-increasing pad; an enzymatic reaction zone; and a top cover (that is, the hydrophilic film).

The conventional fluid test strips are manufactured in batch production by lamination. At first, a conductive electrode layer is printed on a large-size substrate, on which a plurality of electrodes is arranged in an alternating pattern. The number of electrodes included in a single pattern may be varied as desired in practice (for example, a two-electrode pattern or a multi-electrode pattern). Then, an insulating layer provided with a plurality of elongate openings (that is, the structure of the flow channel in the product fluid test strip) is bonded to the substrate printed with the electrode layer, keeping the elongate openings in alignment with the end of the electrode pattern; and a channel is formed in each elongate opening and provided with a test reagent. Afterwards, a top cover provided with a plurality of vent ports is bonded to the insulating layer, which produces a capillary action, whereby the test fluid is sucked via the channel into a test zone for reaction.

The hydrophilic film of the present invention may be directly processed with each functional layer to form an ex vivo membrane. The type of functional layers may be adjusted as desired, and may be, for example, a middle barrier layer, a test layer, an external pattern layer, and so on. The middle barrier layer mainly provides a proper barrier property against the hydrophilic film, and generally has no active reagents or measurement functions. The type of the above-mentioned test layer may depend on the test requirements, and may be, for example, an electrode layer for measuring change in electrical potential. The external pattern layer is correspondingly adjusted according to the requirements of appearance of the ex vivo membrane during fabrication, and mainly provides an aesthetic function.

The present invention also provides a method for producing the hydrophilic film, which comprises the steps of: applying the hydrophilic composition onto a substrate; and curing the hydrophilic composition, wherein the curing method can be heat curing. The method for applying the composition may be selected from the group consisting of gravure coating, die coating, dipping coating, comb coating, spraying, ink-jetting, printing, flexographic printing, heliographic printing, screen printing, and a combination thereof.

The present invention also relates to an ex vivo test strip comprising the above-mentioned hydrophilic film. The ex vivo test strip includes, but is not limited to, a blood glucose test strip, a liver function test strip, a uric acid test strip, and the like.

The hydrophilic film of the present invention has a water contact angle less than 15° and preferably less than 10°, as determined by the ASTM D 7334-08 standard method.

The hydrophilic film of the present invention has a good hydrophilicity maintaining ability. The hydrophilic film of the present invention is found after exposure to elevated temperature and humidity (by standing in a constant temperature and humidity test machine at 65° C./RH 95% for 120 hrs) to have a wetted area that is no less than 75% of that before exposure to elevated temperature and humidity. That is, the difference between the wetted areas prior to and after the test is 0% to 25%. The hydrophilic film of the present invention may have both a low water contact angle)(<15° and a good hydrophilicity maintaining ability (the wetted area is still no less than 75% of the originally wetted area after exposure to elevated temperature and humidity for 120 hrs). The hydrophilic film of the present invention preferably still has a wetted area that is no less than 85% of the originally wetted area, as indicated by the test after exposure to elevated temperature and humidity for 120 hrs.

The hydrophilic film of the present invention has a light permeability of above 70%, as indicated by tests before and after exposure to elevated temperature and humidity following the JIS K7136 standard method, and the difference in light permeability is 0% to 10%, as indicated by tests before and after exposure to elevated temperature and humidity following the JIS K7136 standard method. Thus, the present invention meets the requirements for light permeability in the industry.

The following examples are provided for further illustration of the present invention, and are not intended to limit the scope of the present invention. Any modifications and variations easily made by those of skill in the art are contemplated within the disclosure of the specification and the scope of the appended claims of the present invention.

EXAMPLES

(I) Fabrication of the Membrane

Example 1

25.2 g of Desmodur N3390 (Bayer) was added to a glass reactor. Then, 33 g of 7608 (Momentive) was dissolved in 33 g of ethyl acetate, slowly added dropwise to the glass reactor with stirring at high speed, and heated to 35° C. and reacted for 1 hr after the addition. 90 g of PEG1000 (Sino-Japan Chemical) was added, heated to 65° C. and reacted at this temperature for 5 hrs.

The composition obtained after the reaction was formulated with ethyl acetate to form a coating having a solid content of 0.75% (NV=0.75%), applied onto a PET film (CH885 provided by Nanya Corp., film thickness 100 μm, polyethylene terephthalate) by a RDS coating rod #8, and cured for 5 min by drying at 85° C., to obtain a sheet (hydrophilic film) with a 0.1 μm-thick hydrophilic coating of the present invention. The sheet was measured for the water contact angle, and the water contact angle was measured to be 8.6° on average. Wetting test of the sheet was conducted, and conducted again after exposure to elevated temperature and humidity. The test results are shown in Table 1.

Examples 2-4

Analogous to the fabrication steps in Example 1, a corresponding hydrophilic film was obtained after reaction of the components in the amounts shown in Table 1 and then coating. The test results are also shown in Table 1.

Comparative Example 1

Wetting test of the commercially available 3M 9962 was conducted, and conducted again after exposure to elevated temperature and humidity. The test results are shown in Table 1.

Comparative Examples 2-5

Analogous to the fabrication steps in Example 1, a corresponding hydrophilic film was obtained after reaction of the components in the amounts shown in Table 1 and then coating. The test results are also shown in Table 1.

TABLE 1

Components and their amount (g) and test results of the examples of the present invention and comparative examples

| Component (g) | Example 1 | Example 2 | Example 3 | Example 4 | Comparative Example 1 | Comparative Example 2 | Comparative Example 3 | Comparative Example 4 | Comparative Example 5 |
|---|---|---|---|---|---|---|---|---|---|
| a1 | 25.2 | | 25.2 | 25.2 | — | | | | |
| a2 | | 37.5 | | | — | 20 | | | |
| a3 | | | | | — | | | 8 | |
| a4 | | | | | — | | 15 | | |
| b1 | 33 | 40 | | | — | | 0.6 | | |
| b2 | | | 34.5 | 33 | — | | | 25.3 | 15 |
| b3 | | | | | — | 20 | | | |
| c1 | 90 | | | 11.8 | — | 10 | | | 15 |
| c2 | | 30 | | | — | | | 50 | |
| Wetting test | ○ | ○ | ○ | ○ | X | ○ | ○ | X | ○ |
| Wetting test after exposure to elevated temperature and humidity | ○ | ○ | ○ | ○ | X | X | X | X | X |

Descriptions for Reagents
a1 Desmodur N3390: Polyhexamethylene-based polyisocyanate provided by Bayer
a2 PEG2000 + Karenz AOI: Mixture of polyethylene glycol provided by Sino-Japan Chemical and ethyl isocryanoacrylate provided by Showa (weight ratio 1:14)
a3 Karenz AOI: Ethyl 2-isocryanoacrylate provided by Showa
a4 5036-W-30: Saturated polyester provided by Eternal Material Co., Ltd
b1 7608: Trisiloxane provided by Momentive
b2 (2-Hydroxyethyl)trimethylammonium dimethyl phosphate: (2-Hydroxyethyl)trimethylammonium dimethyl phosphate provided by Alfa Aesar
b3 OT-70: Bis(2-ethylhexyl)succinate sulfonate provided by CYTEC
c1 PEG1000: Polyethylene glycol provided by Sino-Japan Chemical
c2 TMP: Trimethylolpropane provided by ChangChun Corp.

(II) Evaluation of Membrane Performance

1. Hydrophilicity of the Membrane
<Test Method>:
Wetting Test:

3 μl of pure water was pipetted by a micropipette and dripped onto a surface of the hydrophilic film. The diameter of the circle diffused therefrom was measured and recorded. At least 5 measurements were conducted and averaged. The judgment criteria are shown below. The results are shown in Table 1.

○: The average diameter of the circle diffused therefrom is greater than or equal to 6 mm.

X: The average diameter of the circle diffused therefrom is less than 6 mm.

Measurement of water contact angle: The measurement was carried out using a contact angle measurement instrument. During measurement, the sheet was flatly placed on a platform for testing the contact angle, about 3 µl of pure water was dotted on the sample, and the contact angle was recorded (in degrees). At least 5 measurements were conducted and averaged.

2. Hydrophilicity Maintaining Ability of the Membrane

<Test Method>:

Wetting Test after Exposure to Elevated Temperature and Humidity:

A sheet of a hydrophilic film was cut, labeled, exposed to 65° C./RH95% for 120 hrs in a constant temperature and humidity test machine, removed, and cooled for about 30 min. Then, wetting test of the hydrophilic film was conducted. The judgment criteria are shown below. The results are shown in Table 1.

O: The wetted area is greater than or equal to 75% of the originally wetted area (before exposure to elevated temperature and humidity).

X: The wetted area is less than 75% of the originally wetted area (before exposure to elevated temperature and humidity).

(III) Description of the Test Results

It can be known from the data in Table 1 that in Examples 1 to 4, a reactive adhesive and a surfactant having reactivity are used in combination in the hydrophilic composition, such that the membranes have a high hydrophilicity and hydrophilicity maintaining ability with or without the polyol being added, compared with Comparative Example 1 (commercially available 3M 9962 hydrophilic membrane).

A non-reactive surfactant is used in the hydrophilic composition of Comparative Example 2, and a non-reactive adhesive is used in the hydrophilic composition of Comparative Example 3. Due to the absence of crosslinking after curing, the hydrophilic films provided in Comparative Examples 2 and 3 fail to meet the standards in the wetting test after exposure to elevated temperature and humidity; that is, the hydrophilicity maintaining ability is inadequate.

It can be known from the results of Examples 2 and 3 and Comparative Example 4 that although the hydrophilic composition in Comparative Example 4 comprises a reactive adhesive, a surfactant having reactivity, and a polyol, the content of the reactive adhesive is too low (less than 10%), so the coating prepared after curing has insufficient crosslinking, opaque surface, and inadequate hydrophilicity (the water contact angle is 21°), and fails to meet the standards in the wetting tests before and after exposure to elevated temperature and humidity.

The hydrophilic composition of Comparative Example 5 comprises a surfactant having reactivity and a polyol, but no adhesive, such that no crosslinking occurs after curing. It failed to meet the standards in the wetting tests before and after exposure to elevated temperature and humidity.

The foregoing examples are provided as exemplary illustration of the functions and to elucidate the technical features of the present invention, instead of limiting the protection scope of the present invention. All the changes or modifications easily made by any persons of skill in the art without departing from the technical principle and spirit of the present invention are embraced in the scope claimed by the present invention. Therefore, the protection scope of the present invention is defined by the following appended claims.

What is claimed is:

1. A hydrophilic film for an ex vivo membrane, comprising:
   a substrate; and
   a hydrophilic coating located on at least one surface of the substrate and formed by a hydrophilic composition, wherein the hydrophilic composition comprises:
   (a) a reactive adhesive, wherein the reactive adhesive is selected from the group consisting of an isocyanate compound, a melamine compound, and a mixture thereof;
   (b) a surfactant having reactivity, wherein the surfactant comprises a reactive functional group selected from the group consisting of amino, hydroxyl, and a combination thereof;
   (c) optionally a polyol; and
   (d) a solvent, wherein the solvent is selected from an ester, alcohol or ether solvent, water, or a mixture thereof;
   wherein the content of the reactive adhesive is 10 wt % to 60 wt %, based on the total solid content of the composition; the content of the surfactant is 5 wt % to 90 wt %, based on the total solid content of the composition; and the content of the polyol is 0 wt % to 85 wt %, based on the total solid content of the composition, wherein the content of the solvent is 90 to 99.9 wt %, based on the total weight of the hydrophilic composition.

2. The hydrophilic film according to claim 1, wherein the isocyanate compound is a mono-, di-, or polyisocyanate compound and has a group selected from an alkyl group, a phenyl group, a phosphoric acid functional group, a sulfonic acid functional group, an acrylate functional group, or a combination thereof.

3. The hydrophilic film according to claim 1, wherein the surfactant is selected from the group consisting of an ionic emulsifying agent, a nonionic emulsifying agent, and a mixture thereof.

4. The hydrophilic film according to claim 3, wherein a cationic group of the ionic emulsifying agent comprises amino, hydroxyl, or a combination thereof.

5. The hydrophilic film according to claim 4, wherein the cationic group comprises an ammonium or sulfonium group.

6. The hydrophilic film according to claim 3, wherein an anionic group of the ionic emulsifying agent comprises a sulfonic acid group, a phosphoric acid group, a carboxylic acid group, and a combination thereof.

7. The hydrophilic film according to claim 3, wherein the nonionic emulsifying agent is a compound having a siloxanyl group or a polysiloxanyl group.

8. The hydrophilic film according to claim 1, wherein the hydrophilic composition further comprises a curing agent, a curing accelerator, an anti-oxidant, a leveling agent, an inorganic compound, or a combination thereof.

9. The hydrophilic film according to claim 1, wherein the water contact angle of the hydrophilic film is less than 15°, as determined by the ASTM D 7334-08 standard method.

10. The hydrophilic film according to claim 1, wherein the thickness of the hydrophilic coating is 10 nm to 100 µm and the thickness of the substrate is 15 microns to 500 microns.

11. The hydrophilic film according to claim 1, wherein the hydrophilic composition contains the polyol; wherein the content of the surfactant is 10 to 90 wt %, based on the total solid content of the composition.

12. The hydrophilic film according to claim 1, wherein the hydrophilic composition contains no polyol; wherein the content of the surfactant is 50 to 90 wt %, based on the total solid content of the composition.

13. An ex vivo test strip comprising the hydrophilic film according to claim 1.

14. A blood glucose test strip comprising the hydrophilic film according to claim 1.

15. A method for preparing the hydrophilic film according to claim 1, comprising the steps of: applying the hydrophilic composition onto the substrate; and curing the hydrophilic composition.

16. The method according to claim 15, wherein the method for applying the composition is selected from the group consisting of gravure coating, die coating, dipping coating, comb coating, spraying, ink-jetting, printing, flexographic printing, heliographic printing, screen printing, and a combination thereof.

* * * * *